United States Patent [19]

Kéri et al.

[11] Patent Number: 4,855,137

[45] Date of Patent: Aug. 8, 1989

[54] COSMETIC COMPOSITIONS HAVING SKIN CALMING AND SKIN REGENERATING EFFECT AND PROCESS FOR THE PREPARATION THEREOF

[75] Inventors: Tibor Kéri; Jánosné Kristof, both of Debrecen, Hungary

[73] Assignee: Innofinance Altalanos Innovacios Penzintezet, Budapest, Hungary

[21] Appl. No.: 12,875

[22] PCT Filed: May 29, 1986

[86] PCT No.: PCT/HU86/00034

§ 371 Date: Jan. 16, 1987

§ 102(e) Date: Jan. 16, 1987

[87] PCT Pub. No.: WO86/06958

PCT Pub. Date: Dec. 4, 1986

[30] Foreign Application Priority Data

May 30, 1985 [HU] Hungary .............................. 2071/85

[51] Int. Cl.$^4$ .............................................. A61K 35/78
[52] U.S. Cl. .................................................... 424/195.1
[58] Field of Search ..................................... 424/195.1

[56] References Cited

PUBLICATIONS

Lewis, Medical Botany, p. 28.

*Primary Examiner*—John W. Rollins
*Attorney, Agent, or Firm*—Herbert Dubno; Jonathan Myers

[57] ABSTRACT

The invention relates to cosmetic compositions having skin calming and regenerating effect comprising the extract of the aerial shoot and/or tuber of Jerusalem artichoke (Helianthus tuberosus L.) as active ingredient.

10 Claims, No Drawings

COSMETIC COMPOSITIONS HAVING SKIN CALMING AND SKIN REGENERATING EFFECT AND PROCESS FOR THE PREPARATION THEREOF

FIELD OF THE INVENTION

The invention relates to cosmetic compositions having skin calming and skin regenerating effect and a process for the preparation thereof.

BACKGROUND OF THE INVENTION

In the cosmetic industry cosmetic compositions containing the extracts of natural substances (plant or animal organs) as active ingredient have again become popular.

The so called phytocosmetic compositions which belong to this class contain the extracts of various plants, mainly of medicinal plants (among others camomile, burdock, cucumber, lemon etc.) or that of the waste or the valuable parts of the cultivated plants (HU-PS Nos. 178,786 and 179,886, DOS No. 2,641,233).

One characteristic feature of tired skin is a decrease of the easily utilizable sugar content of the cells. According to the GB-PS No. 1,286,156 the loss of the natural sugar content of the skin can be recovered by cosmetic compositions which contain mainly glucose and fructose and optionally ribose, dezoyribose and glucosamine. The composition can be used as a powder or in admixture with the usual cosmetic vehicles.

The aim of the present invention is to prepare cosmetic compositions suitable for calming and regenerating tired, dry skin.

BRIEF DESCRIPTION OF THE INVENTION

During our experiments it has been surprisingly found that the extract of Jerusalem artichoke (Helianthus tuberosus L.) is suitable for the above purpose.

DETAILED DESCRIPTION OF THE INVENTION

The invention relates to cosmetic compositions having skin calming and regenerating effect comprising the extract of the aerial shoot and/or tuber of Jerusalem artichoke as active ingredient together with the usual vehicles and/or diluents and optionally other known additives.

Jerusalem artichoke is a tuberous plant belonging to the compositae, the tuber of which in contrast to the potato does not contain starch but it contains inulin as reserve nutriment. The inulin content of the tuber is about 14 to 16 %. Due to the inulin content of the tubers Jerusalem artichoke is generally used in the food and distilling industry because in the course of the acidic hydrolysis of inulin mainly D-fructose and about 6 % D-glucose are formed. The hydrolysis of inulin takes place faster and more easily than that of potato starch. The hydrolysis takes place also in diluted acetic acid but it is enough to boil the tubers in water for some hours.

The other characteristic feature of Jerusalem artichoke is that in the course of its growth season fungus infections are only rarely observable and the rare infections do not spread (I. Izsó, The Jerusalem artichoke, Akadémiai Kiado, Budapest, 1955). Based on this observation we have examined the extracts of the aerial shoots and it has been found that the extracts show a considerable fungicidal activity against several fungi.

According to the invention extracts are prepared from the aerial shoot and/or tuber of Jerusalem artichoke and the extracts were used separately or in combination as active ingredients of cosmetic compositions. During our experiments it has been found that the extract of the aerial shoot and the syrup prepared from the tuber as well as their combination are remarkably suitable for calming and regenerating tired skin and for treating certain inflammatory conditions.

The favorable effects of the compositions of the invention were examined in the following way.

The face tonic (Example 7) was examined on 50 women aged from 20 to 63 years. It was applied after thorough cleaning twice daily, in the morning and in the evening. The treatment was continued for two weeks. The following types of the face skin were examined: 40 slightly dry, 10 sensitive dry skins. The tonic has been absorbed well during each treatment, the skin became smooth, velvety. During the treatment no allergic reaction, irritative dermatitis or hypersensitivity were observed.

The body lotion (Example 5) was tested on 22 women aged from 19 to 72 years. The lotion was applied after thorough washing twice daily, in the morning and in the evening. The treatment was continued for two weeks. The following types of skin were examined: 2 normal sensitive, 4 dry sensitive, 8 dry and 8 normal skins. The composition has been absorbed well during each treatment, the skin became velvety, smooth, the skin tightening and dryness which occurred after washing (having a bath or shower bath) stopped and the skin was calmed and refreshed. No allergic reaction, irritative dermatitis or hypersensitivity were observed.

The extract of the aerial shoots and the syrup prepared from the tuber can be mixed with the usual cosmetic vehicles and diluents as well as with other known active ingredients e.g. antibiotics, disinfectants, for example propolis and thereby stable compositions are formed.

The compositions are prepared in the following way:

(a) the cleaned and crushed aerial shoot of Jerusalem artichoke is extracted with a 1 to 10-fold amount of water and/or alcohol at a temperature between room temperature and the boiling point of the mixture for from 12 to 168 hours, then the mixture is cooled and filtered, the filtrate (solid substance content is generally about from 0.2 to 6.0 %) is mixed with the usual cosmetic vehicles and/or diluents, preferably with natural fats, oils, waxes, alcohols, emulsifying agents, perfume substances and optionally with other known additives, preferably water binding agents, disinfectants and antibacterial agents and the consistence of the composition thus obtained is adjusted with distilled water and/or alcohol or (b) the washed and sliced tuber of Jerusalem artichoke is extracted with water, the extract is filtered, the filtrate is boiled for from 0.5 to 10 hours, the solution thus obtained is filtered, the filtrate is mixed with the usual cosmetic vehicles and/or diluents, preferably with natural fats, oils, waxes, alcohols, emulsifying agents, perfume substances, and optionally with other known additives, preferably water binding agents, vitamins and antibacterial agents and the consistence of the composition thus obtained is adjusted with distilled water.

If desired the extracts prepared according to the processes (a) and (b) are mixed in a volume ratio between 0.5:1.0 and 2.0:20.0 and the combination is used as active ingredient in cosmetic compositions.

The following non-limiting Examples show the composition of the invention and the preparation of the active ingredient.

EXAMPLE 1

Preparation of an aqueous extract from the aerial shoots of Jerusalem artichoke 1 kg of the cleaned and washed aerial shoot of Jerusalem artichoke is stirred for 8 hours in 10 litres of water at 90° C. Then the mixture is filtered and the filtrate is stored under cooling, protected from light and air.

EXAMPLE 2

Preparation of an alcoholic extract from the aerial shoot of Jerusalem artichoke 1 kg of cleaned and washed aerial shoot of Jerusalem artichoke is allowed to stand for 4 days in 4 litres of 70% aqueous ethanol. The mixture is stirred several times daily, then after 4 days it is filtered and the filtrate is stored under cooling, protected from light and air.

EXAMPLE 3

Preparation of an extract - syrup - from the tuber of Jerusalem artichoke 1 kg of the washed and sliced tuber of Jerusalem artichoke is extracted with 10 litres of water for 12 hours and the extract is filtered. To the filtrate 25 ml of acetic acid are added and the solution is boiled for 30 minutes. Then it is allowed to cool, filtered and stored under cooling.

EXAMPLE 4

| Cream | |
| --- | --- |
| Components | |
| Extract of Example 1 | 25.0 g |
| Cetyl alcohol | 3.5 g |
| Vaseline oil (cosmetic quality) | 8.0 g |
| Propylene glycol | 5.0 g |
| BRIJ J21 | 3.5 g |
| Ethanol (96%) | 4.0 g |
| Nipagine | 0.2 g |
| Stearic acid | 4.0 g |
| Distilled water | 46.8 g |

EXAMPLE 5

| Body lotion | |
| --- | --- |
| Components | |
| Extract of Example 1 | 22.0 g |
| Oleum helianthi | 2.5 g |
| Glycerol | 3.5 g |
| Geranium oil | 0.2 g |
| Nipagine | 0.2 g |
| Sodium dodecylsulfate | 0.6 g |
| Cetyl alcohol | 5.0 g |
| Paraffin oil | 2.0 g |
| Distilled water | 44.0 g |

EXAMPLE 6

| Cream | |
| --- | --- |
| Component | |
| Extract of Example 1 | 21.0 g |
| Extract of Example 3 | 3.5 g |
| Cetyl alcohol | 1.0 g |
| BRIJ J2 | 2.3 g |

| Cream (continued) | |
| --- | --- |
| Vaseline oil (cosmetic quality) | 8.0 g |
| Ethanol (96%) | 6.0 g |
| Nipagine | 0.2 g |
| Isopropyl palmitate | 6.0 g |
| Distilled water | 52.0 g |

EXAMPLE 7

| Cream | |
| --- | --- |
| Components | |
| Extract of Example 2 | 25.5 g |
| Extract of Example 3 | 4.0 g |
| Erythromycin base | 2.0 g |
| Cetyl alcohol | 1.5 g |
| Vaseline oil (cosmetic quality) | 7.5 g |
| Ethanol (96%) | 4.5 g |
| Nipagine | 0.2 g |
| Propylene glycol | 5.0 g |
| Distilled water | 49.8 g |

EXAMPLE 8

| Face tonic | |
| --- | --- |
| Components | |
| Extract of Example 2 | 27.0 g |
| Propylene glycol | 8.0 g |
| Tween 20 | 0.5 g |
| Ethanol (96%) | 64.3 g |
| Perfume oil | 0.2 g |

We claim:

1. A cosmetic composition having a skin-calming and skin-regenerating effect comprising as active ingredient, an aqueous or alcoholic extract of the aerial shoot, tuber, or aerial shoot and tuber of a Jerusalem artichoke in an amount of 1.0 to 50% together with a pharmaceutically acceptable topical inert carrier or diluent.

2. The cosmetic composition having a skin-calming and skin-regenerating effect defined in claim 1 further comprising a water-binding agent.

3. The cosmetic composition having a skin-calming and skin-regenerating effect defined in claim 1 further comprising a vitamin.

4. The cosmetic composition having a skin-calming and skin-regenerating effect defined in claim 1 further comprising a disinfectant.

5. The cosmetic composition having a skin-calming and skin-regenerating effect defined in claim 1 further comprising an antibacterial agent.

6. The cosmetic composition having a skin-calming and skin-regeneratig effect defined in claim 1 comprising as active ingredient a mixture of the extracts of the aerial shoot and tuber of the Jerusalem artichoke wherein the volume ratio of the extract of the aerial shoot to that of the tuber is between 0.5:1.0 and 2.0:20.0.

7. A process for the preparation of a cosmetic composition having a skin-calming and skin-regenerating effect which comprises the steps of:
(a) cleaning and crushing aerial shoots of Jerusalem artichoke;
(b) extracting the cleaned and crushed aerial shoots of Jerusalem artichoke with a 1 to 10 fold amount of water, ethanol, or a mixture of water and ethanol, at a temperature between room temperature and the boiling point of the mixture for 12 to 168 hours;
(c) cooling the extract;
(d) filtering the extract to obtain a filtrate; and
(e) combining the filtrate with a pharmaceutically acceptable inert carrier or diluent.

8. A process for the preparation of a cosmetic composition having a skin-calming and skin-regenerating effect which comprises the steps of:
(a) washing and slicing a tuber of Jerusalem artichoke;
(b) extracting the washed and sliced Jerusalem artichoke with water;
(c) filtering the extract formed during step (b) to obtain a filtrate;
(d) boiling the filtrate for 0.5 to 10 hours;
(e) filtering the boiled filtrate to obtain a second filtrate; and
(f) combining the second filtrate with a pharmaceutically acceptable inert carrier or diluent.

9. A method of treating the skin of a susceptible subject to impart a velvety and smooth texture thereto, said method comprising the step of applying to the skin a cosmetic composition containing an effective amount of an aqueous or alcoholic extract of the aerial shoot or tuber of the Jerusalem artichoke in a plurality of applications.

10. The method defined in claim 9 wherein said extract is a mixture of an extract of said aerial shoot with an extract of said tuber.

* * * * *